(12) United States Patent
Ragsdale

(10) Patent No.: US 7,428,322 B2
(45) Date of Patent: Sep. 23, 2008

(54) IMAGING METHOD AND APPARATUS

(75) Inventor: Charles W. Ragsdale, Concord, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 706 days.

(21) Appl. No.: 10/829,407

(22) Filed: Apr. 20, 2004

(65) Prior Publication Data

US 2006/0274922 A1 Dec. 7, 2006

(51) Int. Cl.
*G06K 9/00* (2006.01)
(52) U.S. Cl. .................. 382/128; 382/274; 702/20
(58) Field of Classification Search .............. 382/107, 382/115, 118, 128, 129, 133, 134, 168, 169, 382/170, 172, 203, 209, 219, 260, 274; 435/287.2, 435/6, 226; 702/19, 20; 378/2
See application file for complete search history.

(56) References Cited

U.S. PATENT DOCUMENTS

| | | | |
|---|---|---|---|
| 5,719,951 A * | 2/1998 | Shackleton et al. ......... 382/118 |
| 6,489,159 B1 * | 12/2002 | Chenchik et al. ......... 435/287.2 |
| 6,607,888 B2 * | 8/2003 | Schwartz et al. ............... 435/6 |
| 6,671,625 B1 * | 12/2003 | Gulati ......................... 702/20 |
| 6,727,066 B2 * | 4/2004 | Kaser .............................. 435/6 |
| 6,804,385 B2 | 10/2004 | Eisfeld et al. |
| 6,872,560 B1 * | 3/2005 | Yue et al. ..................... 435/226 |
| 6,920,397 B2 * | 7/2005 | Gulati ......................... 702/19 |

* cited by examiner

*Primary Examiner*—Seyed Azarian
(74) *Attorney, Agent, or Firm*—Townsend and Townsend and Crew LLP

(57) ABSTRACT

A method is provided for measuring a response to a stimulus of a plurality of samples spots of a sample using a measuring system having a measurement range to generate an image of the sample in digital space. The method includes, for each sample, while measuring the response, varying the stimulus to include at least one stimulus value where the measured response corresponds to a value in an intermediate portion of the measuring range, and storing a value of the measured response that corresponds to a value in the intermediate portion of the measurement range, and the stimulus value that produced that value of the measured response.

42 Claims, 8 Drawing Sheets

IMAGING METHOD AND APPARATUS

BACKGROUND OF THE INVENTION

The present invention relates to imaging samples and more particularly relates to image samples having a response range that exceeds the measurement range of an imaging system.

Samples that have response ranges that exceed the measurement range of imaging detectors include microarray samples as well as other sample types. A microarray is a tool for analyzing gene expression, such as for matching known and unknown DNA samples, complementary DNA (cDNA) samples, and messenger RNA (mRNA) samples based on base-pairing rules. Nearly every cell of a human body contains a full set of chromosomes and identical genes. At any given time, a fraction of these genes is turned on to perform their genetic purpose. The fraction of genes in a cell that is turned on is typically referred to as being "expressed," and "gene expression" refers to the subset of genes that is expressed that confers unique properties to each cell type. The term gene expression also refers to the transcription of information contained within DNA into mRNA molecules that are then translated into the proteins that perform the majority of cell functions. The types and amounts of mRNA produced by a cell are studied to identify the particular genes that are expressed, which in turn, provides insight into the ways cells respond to changing environments, changing needs, mutations, and the like. Gene expression is a complex and tightly regulated process that allows a cell to respond dynamically both to environmental stimuli and to its own changing needs. This process acts as both an "on/off" switch to control the genes that are expressed in a cell as well as a "volume control" that increases or decreases the level of expression of particular genes. Microarrays and microarray imaging provide for the detection of genes that are expressed, as well as for the detection of how strongly genes are expressed.

A microarray typically includes a small support structure onto which the sequences of a number of different known genes are immobilized at fixed locations. These genes are known as probes to which target genes (or targets) might attach. The probes might include DNA, cDNA, or oligonucleotides. An oligonucleotide (or oligo) is a relatively short fragment of a single-stranded DNA that is typically five to fifty nucleotides long. A target may include known and/or unknown DNA, cDNA, mRNA or the like. Support structures often include glass microscope slides, silicon chips, or nylon membranes. The probes may be printed or synthesized directly on a support structure to form the microarray spots of a microarray. Targets that attach with the probes allow researchers to optically identify the targets and the genes that are expressed by a cell and the strength of the expression.

The performance of a microarray experiment is based on hybridization probing. Hybridization probing typically includes targets tagged with fluorescent chromophores to identify complementary probes and targets that are able to base pair with one another. Complementary probes and targets (sometime referred to as mobile probes) are incubated to allow complementary gene sequences to bond together (or hybridize). Bound targets are typically identified using a laser excitation process that causes the fluorescent tags in the targets to fluoresce, emitting known radiation wavelengths that might be in the red and/or green spectral bands. A first excitation-spectral band is often used to excite one set of fluorescent tags coupled to one set of targets and a second excitation-spectral band is often used to excite another set of fluorescent tags coupled to another set of targets. The sets of target may be from a known control sample and a sample having unknown targets. Fluorescent emission (or emission) from the targets provides for the identification of the targets in a sample, as each spot in a microarray includes a known probe that might hybridize with a known complementary target. Moreover, a ratio, for example, of red and green emissions from microarray spots might be used to determine differences in gene expressions, such as gene mutation and the like.

FIG. 1 is a simplified image of a microarray that includes a number of image spots of microarray spots having various emission intensities. As mentioned briefly above, each microarray spot is associated with a particular gene sequence. The image spot locations, relative brightness of the image spots, and/or the colors of the image spots provide an estimate of the gene expression associated with a sample, such as the mRNA of a cell.

Microarray images and images of other samples are typically generated by imaging systems having detectors with fixed measurement range. Emissions from microarray spots often fall within a range of intensities that exceed the fixed measurement range of imaging systems. For example, emission intensities might extent below a threshold detection level and/or above a saturation level of a detector, such as a detector that includes an analog-to-digital (A/D) converter having a fixed measurement range. While imaging systems can be modified to include analog-to-digital converters that have increased measurement ranges, such solutions are often costly. For example, if a detector that includes an A/D converter having, say a 12-bit output, is to be changed with an A/D converter having a 32-bit output or a 64-bit output, many components of an imaging system might be updated to accommodate the increased measurement range of the new A/D converter. For example, in addition to changing the A/D converter, a new detector boards on which the new A/D converter is installed might me changed, or an entire computing platform of an imaging system might even be changed to accommodate the increased measurement range of the new A/D converter. Such modifications are costly not only due to the cost of the new components, but are also costly because the imaging system may be unavailable for use during the upgrade period. Moreover, while changing a detector's AID converter may provide an output having a higher bit width, a higher bit width A/D converter may provide a signal wherein the additional bits do not provide increased sample information, but provide bits that represent noise. Accordingly, it is desirable to provide techniques wherein a sample is sufficiently stimulated such that the sample response is sufficiently above the background noise level of the detector to produce a meaningful result and not merely increased noise.

A number of techniques have been used to image samples while avoiding changing detector components (e.g., A/D converters) in imaging system, but tend to be slow and computationally intensive. For example, one traditional technique for collecting a wide range of emission intensities from a sample, and hence collecting a relatively complete set of image data for a sample, using a detector that has a limited analog-to-digital measurement range, includes scanning the sample a sample a number times with different radiation intensities and/or with a radiation detector (e.g., a photomultiplier tube) set to different sensitivity levels for each sample scan. Varying radiation intensity and/or detector sensitivity provides that the measurement range of a detector's A/D converter is not exceeded. However, scanning a sample multiple times typically take a relatively long time. For example, ten scan might be used to collect a relatively full set of image data for a sample. As each scan might take, for example, thirty to fifty minutes, ten scans of the sample will take at least three hundred minutes to five hundred minutes. The time to collect a set of image data might even take longer than this as these times do not take into account the time for changing the radiation intensity of the radiation source and/or adjusting the sensitivity level of a radiation detector.

The foregoing described techniques for collecting a relatively full set of image data for a sample introduce additional difficulties. For example, as sample-scanning times are increased, the increased time of radiation exposure tends photobleach a sample. Therefore, a sample for each scan is not really the same, but has a varying baseline response. Various algorithms might be applied to image data to correct for photobleaching, but such algorithms tend to be complicated and time consuming.

Accordingly, new methods and apparatus are needed for the generation of images of samples using an imaging system having a detector with an A/D converter having a fixed measurement range, wherein sample responses exceed the measurement range of the AID converter.

BRIEF SUMMARY OF THE INVENTION

Embodiments of the present invention provide a method and system for generating images of samples, and more particularly provide a method and system for the generation of an image of a sample, such that the image is generated by in a single scan of the sample by measuring the response to a stimulus of a plurality of sample spots using a measuring system having a measurement range, such that the responses are in an intermediate measurement range of the measuring system and are normalized by a set of stimulus values associated with the response and that are scaled by a highest stimulus value for the responses, such that the normalize and scaled responses exceed the measurement range and form the image in digital space.

According to one embodiment, a method is provided for measuring a response to a stimulus of a plurality of samples spots of a sample using a measuring system having a measurement range to generate an image of the sample in digital space includes for each sample, while measuring the response, varying the stimulus to include at least one stimulus value where the measured response corresponds to a value in an intermediate portion of the measuring range, and storing a value of the measured response that corresponds to a value in the intermediate portion of the measurement range, and the stimulus value that produced that value of the measured response. According to a specific embodiment, the method further includes dividing each stored value of the measured response by the corresponding stimulus value to provide a normalized-response value. According to another specific embodiment, the method further includes, for each normalized-response value, multiplying each normalized-response value by a highest stimulus value that is stored to generate the image, wherein these normalized-response values that are multiplied by the highest stimulus value that is stored are referred to as the image spots. The image spots form the image in digital space. According to another specific embodiment, the steps of varying the stimulus and storing the value of the measured response are performed in one scan of the sample. According to another specific embodiment, the measuring system includes an A/D converter having a particular number of bits that accommodates a particular range of response values. And at least one of the image spots has a number of bits that exceeds the particular number of bits of the A/D converter. According to a specific embodiment, the samples spots are regions having probes hybridized with targets having fluorescent tags; the stimulus is visible or UV optical radiation; and the response is a level of fluorescent emission.

According to another embodiment, a method is provided for acquiring image-response values for an extended sample subjected to a stimulus to generate an image in digital space that includes the image-response values. The method include for each of a plurality of spots, subjecting the sample to a plurality of stimulus values in a single scan of the spots, measuring corresponding response values, determining a stimulus value that provides a response value within a desired range, and storing the stimulus value, so determined, and the response value provided by that stimulus value; providing a normalized data set for the plurality of spots where each spot's normalized value represents a ratio of the stored response value and the corresponding stimulus value. According to a specific embodiment, the step of providing the normalized data set for the plurality of spots includes multiplying the normalized values by a highest stored stimulus value, and these values are the image-response values. According to another specific embodiment, the desired range is an intermediate range of an A/D converter having a particular number of bits that accommodates a particular range of response values, and at least one of the image-response values has a number bits that exceeds the particular number of bits of the A/D converter.

According to another embodiment, a method is provided for generating a microarray image of a sample that includes a plurality of microarray spots irradiated with laser radiation, such that radiation from each microarray spot is a response to being irradiated. The method includes for each microarray spot in a single scan of the microarray: varying an intensity value of the laser radiation within a range of values, storing a radiation value for the radiation, and a corresponding intensity value for that radiation value, wherein the radiation value is below a saturation level of a detector, and dividing the stored radiation value by the stored intensity value to generate a normalized-radiation value; and multiplying the normalized-radiation values by a highest radiation value that is stored. According to a specific embodiment, the detector includes an A/D converter configured to generate the radiation values, and the saturation level is a saturation level of the A/D converter. The normalized-radiation values multiplied by the highest radiation value this is stored are independent of a measurement range of the A/D converter.

According to another embodiment, an image generator is provided for generating a digital-space image of a sample. The generator includes a radiation source configured to generate radiation and irradiate sample spots of the sample, wherein the sample spots radiate in response to being irradiated; a modulator configured to modulate an intensity of the radiation; a detector having a measurement range and configured to generate radiation values from the radiation from the sample spots; a memory configured to store a radiation value that corresponds to an intermediate portion of the measurement range, and a radiation value for the generated radiation that corresponds to that radiation value; and a processor configured generate image spots of the digital-space image by normalizing the stored radiation values by their associated radiation values of the generated radiation and multiplying these values by a highest radiation value of the generated radiation this is stored the digital-space image. According to a specific embodiment, the detector includes an analog-to-digital (A/D) converter configured to generate the radiation values, and the intermediate portion of the measurement range is an intermediate portion of the measurement range of the A/D converter. According to another specific embodiment, the A/D converter has a particular number of bits that accommodates a particular range of radiation values, and at least one of the image spots has a number bits that exceeds the particular number of bits of the A/D converter. The image spots are independent of a measurement range of the A/D converter. According to a further embodiment, the system further includes a second laser configured to irradiate the sample spots with laser radiation having a wavelength different from the laser radiation of the first mentioned laser to generate a second microarray image.

A further understanding of the nature and advantages of the present invention may be realized by reference to the remaining portions of the specification and the drawings.

DETAILED DESCRIPTION OF THE INVENTION

Figure 1:
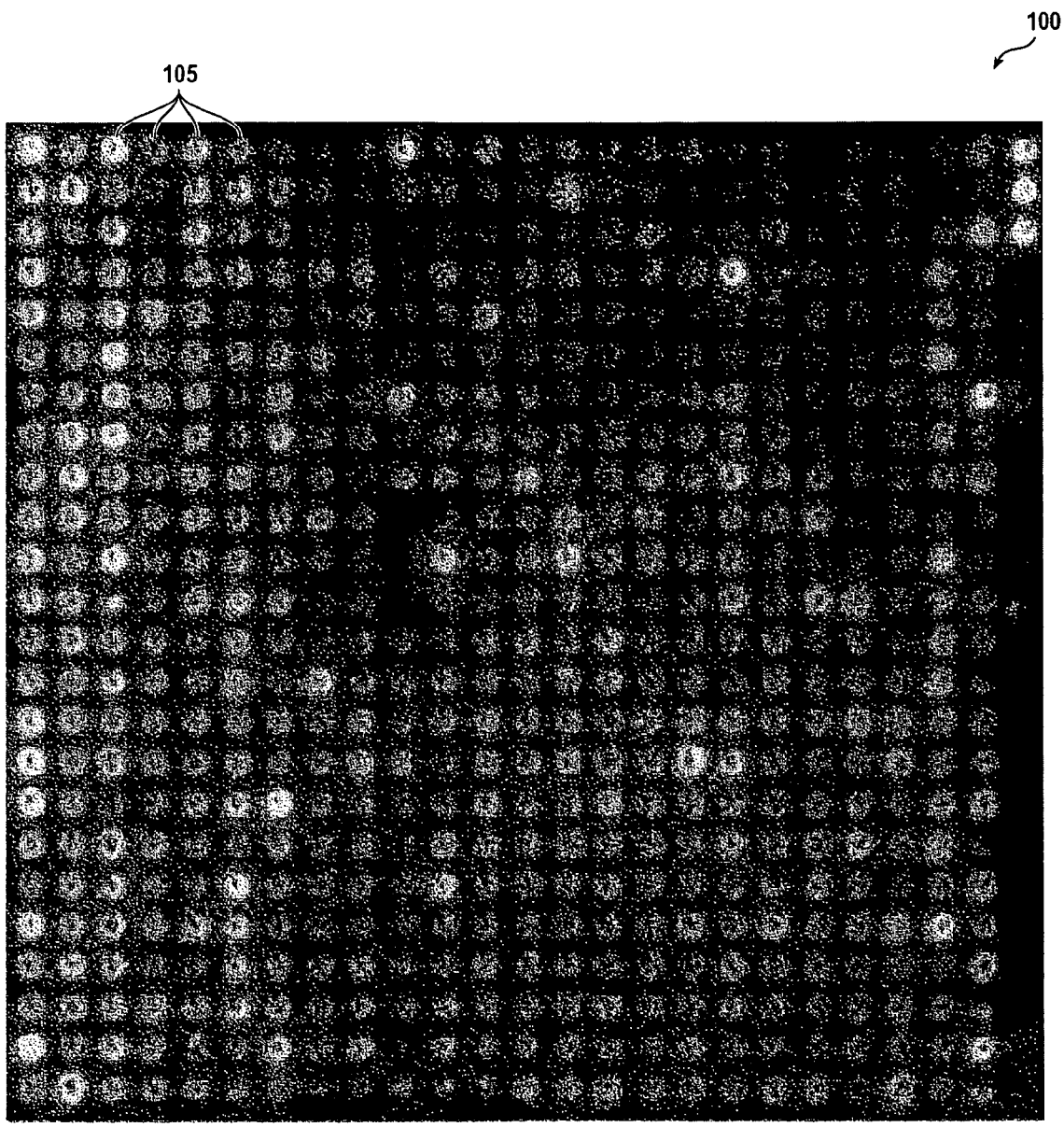
FIG. 1 is a simplified image of a microarray and that includes a number of image spots of microarray spots having various radiation intensities.

The present invention provides an imaging system and imaging technique for generating an image of a sample, and more particularly provides an imaging system and an imaging technique for forming an image from a set of digital-image data by various scanning techniques, such as excitation and fluorescent emission, back scattering, transmission processes (e.g., absorption or forward scattering) or the like, such that the digital-image-data set is generated in a single scan of the sample and is subsequently normalized and scaled to a range that exceeds the measurement range of a detector, such as the measurement range and output bit width of an analog-to-digital converter.

Embodiments of the present invention may be used for generating images of a variety of sample types, such as microarrays, tissue samples, fluid samples, chemical samples, plant samples, or other sample types. While embodiments of the present invention are of use for imaging a variety of sample types, the present description describes a number of exemplary embodiments of the present invention as applied to microarrays and the generation of microarray images. Those of skill in the art, after review of the present description, claims, and attached figures, will know of the broad applicability of embodiments of the present invention to a diversity of sample types (not merely microarrays) that may be imaged according to the embodiments described herein and particularly below.

Microarrays include a number of microarray spots that include probes, such as gene probes, to which targets, such as complementary-genes target, hybridize. Hybridization generally refers to the formation of complementary probes and targets (sometimes referred to as mobile probes). A probe might include DNA, cDNA (complementary DNA), or oligonucleotides. An oligonucleotide (or oligo) is a relatively short fragment of a single-stranded DNA that is typically five to fifty nucleotides long. A target might include DNA, cDNA, mRNA (messenger RNA) or the like that is included in a sample. Various samples might include known and/or unknown targets. Microarray images of samples having known targets, such as healthy targets, might be compared with samples having unknown targets, including, for example, mutated genes to detect the mutation. Such a comparison might be a diagnostic technique for the sample having unknown targets.

To generate a microarray image, a set of digital-image data is generated for a microarray. The digital-image data may include radiation intensity information (e.g., fluorescent emissions, backscattered radiation, transmitted radiation, etc) for an irradiated microarray, and the microarray image may be formed from the digital-image data in digital space, such as the digital space of a computer. Traditionally, digital-image data of a microarray has been generated by scanning the microarray spots a number of times with a number of laser intensities. Multiple scans of a microarray are typically performed due to the limited measurement range of detectors configured to generate the digital-image data. Specifically, multiple scans of microarrays have traditionally been performed as the measurement range and the digital-bit width of analog-to-digital converters, which are configured to generate the digital-image data, are often not sufficiently broad to collect and digitize the full range of radiation intensities from a sample irradiated using a single radiation intensity from a radiation source, or with a radiation detector set at a single sensitivity level. Therefore, these traditional techniques are not configured to generate set of digital-image data of a sample that represents a relatively full range of radiation intensities in a single microarray scan. Moreover, each time a microarray is scanned, the microarray spots tend to photodegrade. More specifically, the tags coupled to the targets tend to photobleach as radiation exposure times are increased. Photobleaching generally refers to an electromagnetic radiation induced change in a chromophore, resulting in the loss of its absorption of the electromagnetic radiation at a particular wavelength. Additionally, as a single scan of a microarray may take from a few minutes to several minutes, scanning the microarray several times compounds the length of time in which a final microarray image might be generated. Embodiments of the present invention are configured to address the foregoing described problems as well as other problems, which will be readily apparent on review of the instant specification and accompanying drawings.

Figure 2:
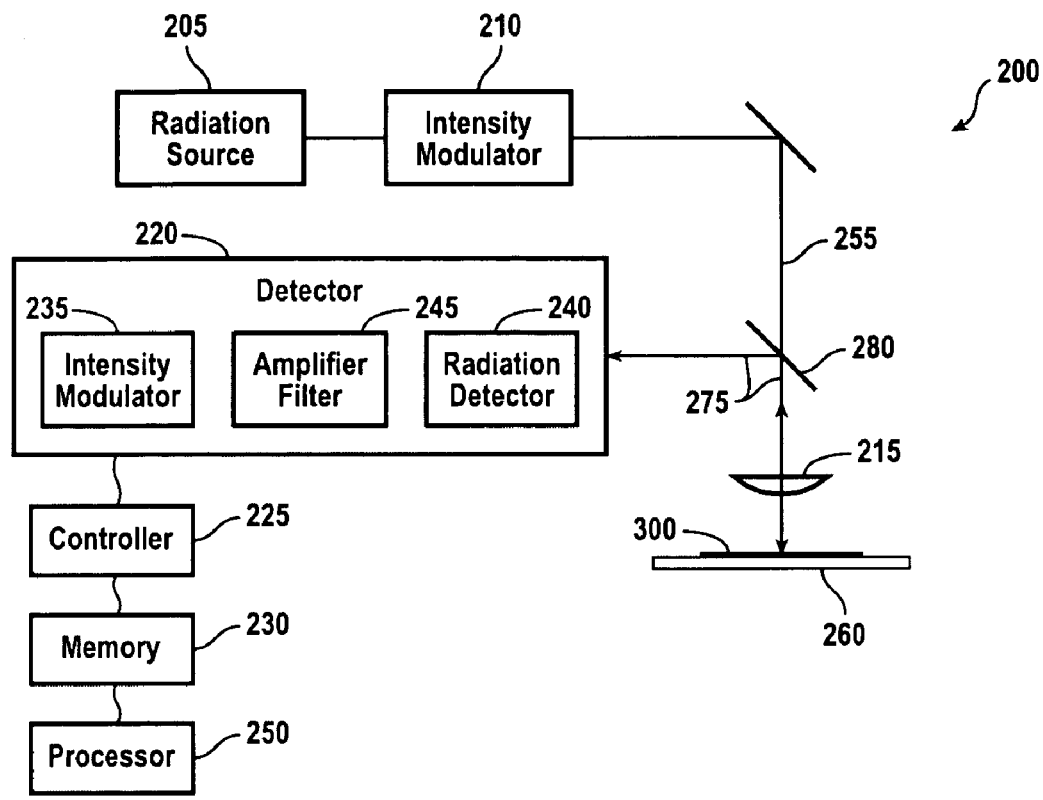
FIG. 2 is a simplified block diagram of an imaging system 200 according to an embodiment of the present invention.

FIG. 2 is a simplified block diagram of an imaging system 200 configured to generate images of a sample according to an embodiment of the present invention. Imaging system 200 might be a microarray-imaging system configured to generate microarray images, for example, in digital space. According to one embodiment, imaging system 200 includes an electromagnetic-radiation (or radiation) source 205, an intensity modulator 210, a set of lenses 215, a detector 220, a controller 225, and a memory 230. As referred to herein, a set includes one or more elements. For example, the set of lenses 215 might include one or more lenses. For example, the set of lenses may include a single objective lens or a number of lenses that form an objective lens system. According to some embodiments, detector 220 includes an analog-to-digital (A/D) converter 235. According to a further embodiment, detector 220 includes an electromagnetic radiation detector (or radiation detector) 240. According to yet a further embodiment, detector 220 includes an amplifier-filter module 245. While FIG. 2 shows that detector 220 includes a radiation detector, an A/D converter, and an amplifier-filter module, it should be understood that various embodiments of the present invention may not include each of these three modules, and may include other modules that would be readily apparent to those of skill in the art. According to some embodiments, imaging system 200 includes a processor 250. Radiation source 205 may include one or more of a variety of radiation sources, such as (but not limited to) a laser, a gas discharge tube, a blackbody radiator (e.g., a light bulb), a fluorescent light source or other radiation sources. Radiation as referred to herein may include any wavelength or combination of wavelengths of electromagnetic radiation, such as infrared radiation, visible light, or ultraviolet radiation. Also as referred to herein, light may include any wavelength or combination of wavelengths of electromagnetic radiation, such as infrared radiation, visible light, or ultraviolet radiation, and is not limited to electromagnetic radiation that is visibly perceptible.

Figure 3:
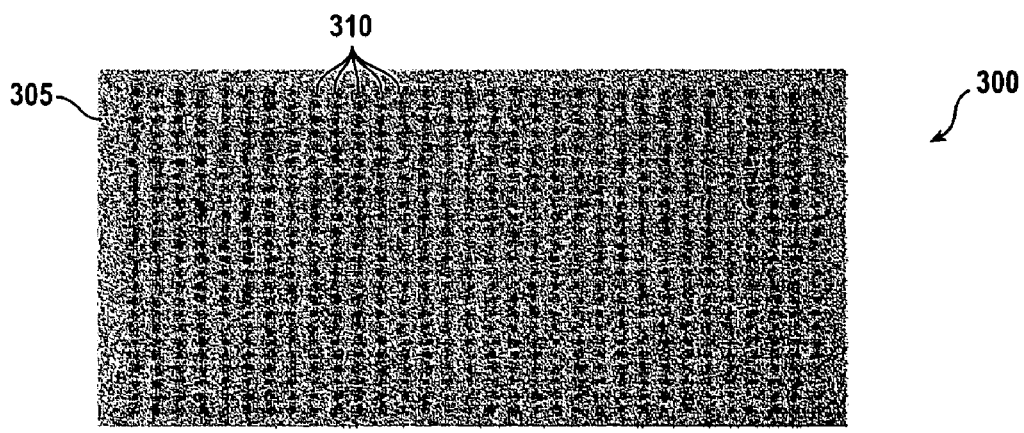
FIG. 3 is a simplified layout drawing of a microarray that includes a substrate on which a set of microarray spots is formed.

According to one embodiment, imaging system 200 is configured to generate microarray images of a microarray. FIG. 3 is a simplified layout drawing of an exemplary microarray 300 that includes a substrate 305 on which a set of microarray spots 310 is formed. Each microarray spot includes a probe to which a target might hybridize. The probes might be printed, or might be synthesized directly on the support, to form the microarray spots of the microarray. FIG. 1 is a simplified microarray image 100 that includes a number of image spots 105 that might correspond to a number of microarray spots 310, and might be a microarray image that is generated by imaging system 200. FIG. 1 is a graphical representation of digital-image data that might be generated for a microarray and that may be stored in memory 230. Each image spot may have a different brightness and/or color that corresponds to the radiation intensities and/or colors of the microarray spots irradiated by radiation 255 (e.g., laser radiation) of radiation source 205. The relative brightness of the image spots and/or their colors provide an estimate for target concentrations in a sample, and in turn, may provide an estimate of a cell's gene expression. It should be understood that microarray image 100 and microarray 300 are shown for exemplary purposes. Microarrays and microarray images, according to other embodiments of the present invention, may have different numbers of microarray spots and image spots.

Imaging system 200 is configured to irradiate rows of microarray spots with radiation 255, for example, via a raster scan. According to one embodiment, microarrays (or other sample types) are scanned a single time by imaging system 200 to generate a microarray image. Stated alternatively, according to embodiments of the present invention (described in detail below), in a single scan of a microarray (or other sample type) a relatively complete set of digital-image data is generated for the formation of a microarray image (e.g., in digital space). As a relatively complete set of digital-image data is generated in a single scan of a microarray, subsequent scans might not be performed.

While imaging system 200 is described herein as being configured to irradiate discrete microarray spots of a microarray (e.g., in a raster scan), imaging system 200 may also be configured to irradiate select areas (that might also be referred to as spots) of a sample, wherein the sample is a relatively continuous sample (e.g., a tissue cross section), but wherein the select areas may or may not be contiguous. According to one embodiment, lens 215 may be configured to raster along the rows of microarray spots to sequentially (or otherwise) irradiate the microarray spots with radiation 255. Means for rastering lens 215 are not shown or described herein as such means are well known to those of skill in the art. Each row may be moved into a position for scanning by a stage 260. Radiation 255 may be excitation radiation that is configured to excite tags coupled to the targets, such that the excited tags emit fluorescent radiation. Alternatively, the radiation from the microarray spots (or spots of other sample types) may be backscattered radiation or transmitted radiation, such as the radiation of a transmission spectrum (e.g., if the radiation configured to irradiate a sample is multi-spectral radiation), forward scattered radiation or the like.

Figure 4:
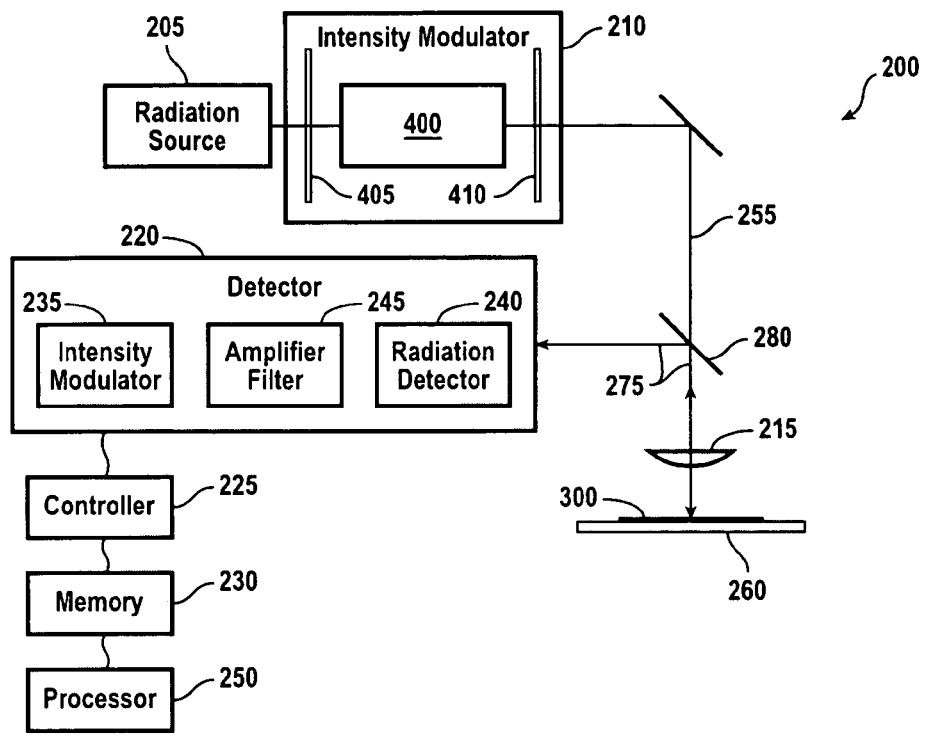
FIG. 4 is a simplified schematic of an intensity modulator that includes an electrooptic modulator (e.g., a lithium niobate crystal) disposed between crossed polarizers according to an embodiment of the present invention.
Figure 5:
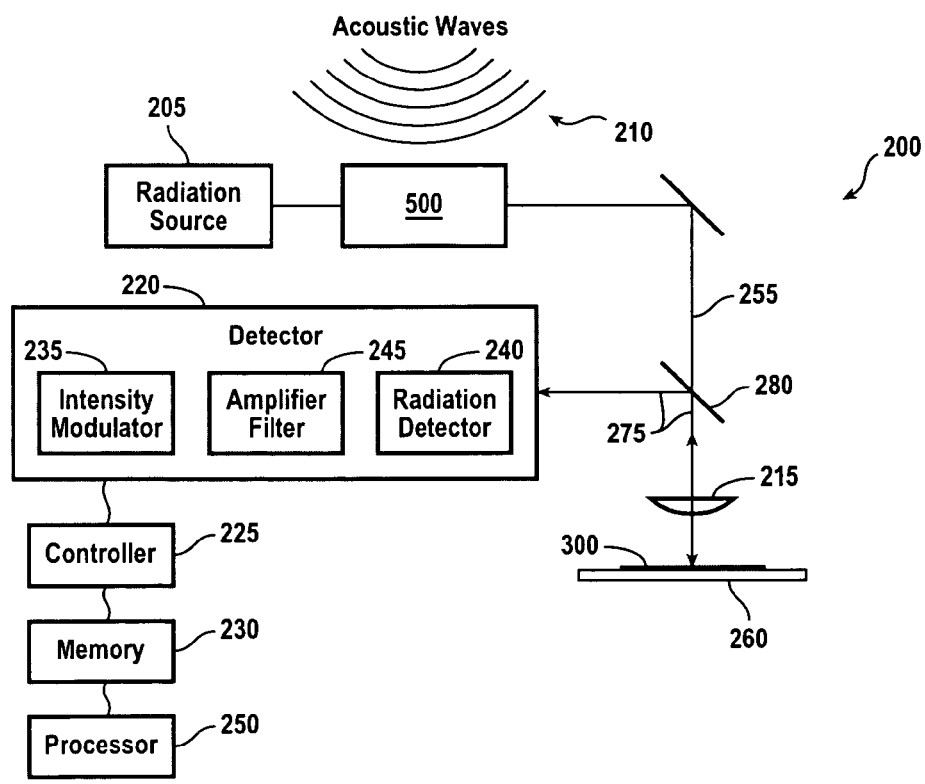
FIG. 5 is a simplified schematic of an intensity modulator that includes an acoustooptic modulator according to another embodiment of the present invention.
Figure 6A:
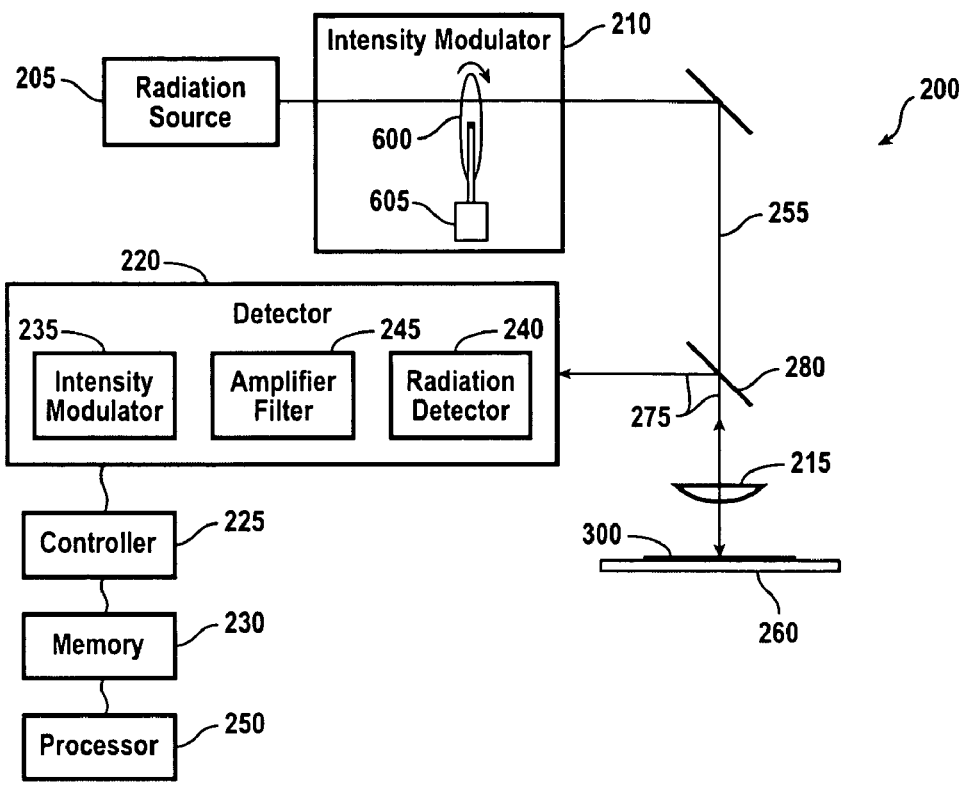
FIG. 6A is a simplified schematic of an intensity modulator that includes a graded-neutral-density filter coupled to a controller that may include a galvanometer, or the like, that is configured to move the graded-neutral-density filter through the laser radiation along a filter gradient to modulate the laser-radiation intensity according to another embodiment of the present invention.
Figure 6B:
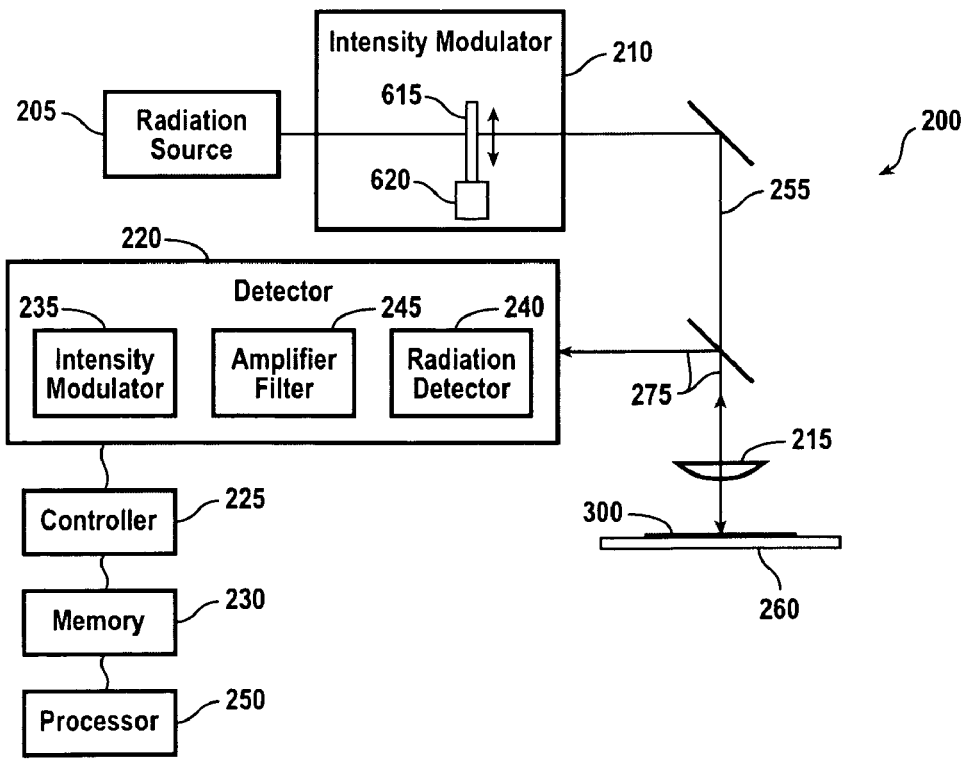
FIG. 6B is a simplified schematic of an intensity modulator that includes a graded-neutral-density filter coupled to a controller, wherein the controller includes a piezoelectric device, or the like, that is configured to move the graded-neutral-density filter through the laser radiation along a filter gradient to modulate the laser-radiation intensity according to another embodiment of the present invention.

According to one embodiment, as each spot of a microarray (or other sample type) is irradiated with radiation 255, the intensity of radiation 255 is modulated. The intensity of the radiation is modulated by intensity modulator 210. While intensity modulator 210 is shown in FIG. 2 as varying the intensity of radiation 255 subsequent to emission from the radiation source, the intensity modulator may be configured to vary one or more parameters of the radiation source, such that the radiation emitted by the radiation source is varied in intensity. For example, the intensity modulator may be a device configured to vary the current supply of a radiation source that includes a laser, such as a diode laser, to vary the intensity of the laser radiation generated by the diode laser. Intensity modulator 210 may include a variety of devices configured to modulate radiation intensity. For example, the intensity modulator may include an electrooptic modulator (e.g., a lithium niobate crystal) 400 disposed between crossed polarizers 405 and 410 as shown in FIG. 4. Alternatively, the intensity modulator may include an acoustooptic modulator 500 configured to modulate radiation intensity subsequent to emission of the radiation from the radiation source, as shown in FIG. 5. The intensity modulator may include a graded-neutral-density filter and a controller configured to move the graded-neutral-density filter through the radiation beam along a filter gradient to modulate the radiation intensity. In FIG. 6A, the intensity modulator is shown to include a graded-neutral-density filter 600 coupled to a controller 605 that may include a galvanometer, or the like. In FIG. 6B, the intensity modulator is shown to include a graded-neutraldensity filter 615 coupled to a controller 620 that may include a piezoelectric device or the like. According to some embodiments, the intensity modulator includes an optical chopper (not shown) that is configured to chop the radiation to generate temporal windows in which microarray spots are alternately irradiated, and then not irradiated. According to one embodiment, temporal lengths of radiation windows are longer than excitation delays of the targets' fluorescent tags. For example, an optical chopper may be configured to irradiate a microarray spot for about 10 nanoseconds up to 100 microseconds, for a tag having a fluorescent emission time, for example, of about 2-3 nanoseconds.

Radiation 275 from the irradiated microarray spots might be focused on the radiation detector by lens 215, and might be directed to the detector by a beam splitter 280 and/or other optical-routing device. Radiation 255 and radiation 275 are sometimes referred to herein respectively as the stimulus and the response. Radiation 275 is collected by radiation detector 240 that is configured to generate analog signals for the detected radiation. These analog signals that are the radiation-detector output are digitized by A/D converter 235. According to one embodiment, the analog signals generated by the radiation detector are amplified and filtered by amplifier-filter module 245 prior to being digitized. Radiation detector 240 may include a photomultiplier tube, an avalanche photodiode, a CCD (charge coupled device) array, a CMOS (complementary metal oxide) array or other detectors in use at the time.

According to one embodiment, digitized-radiation values (or radiation values) generated by the A/D converter are monitored by controller 225 (and/or processor 245) as the intensity of radiation 255 is modulated by intensity modulator 210. The controller is configured to control storage of the radiation values in memory 235. The controller may control storage of a radiation value for each microarray spot, such that these radiation values correspond to an intermediate portion of the measurement range of detector 220. For example, the controller may control storage of a radiation value for each microarray spot, such that these radiation values correspond to an intermediate portion of the measurement range of A/D converter 235. Stated alternatively, for radiation values stored in memory, the analog output of radiation detector 240 (or amplifier-filter module 245) is in an intermediate portion of the A/D converter's measurement range (explained in further detail below with respect to the example of Table 1). The intermediate portion of the A/D converter's measure range may include a range of about +/−20% (inclusive) of a predetermined measurement level, such as an approximately central measurement level (i.e., a measurement level that is approximately in the middle of the A/D converter's measurement range). In addition to storing these radiation values in the memory, radiation-intensity values for radiation 255 (e.g., excitation values) that respectively correspond to these radiation values are also stored in the memory. Associated radiation values and radiation-intensity values may be stored in memory locations that correspond to the positions of associated microarray spots on a microarray. For example, a memory location (or the memory location's address) configured to store an associated radiation value and a radiation-intensity value may correspond to the x- and y-coordinates of the microarray spot associated with these values. Storing radiation values and radiation-intensity values in such a manner, provides that the x- and y-coordinate information for the microarray spots is preserved, although the actual values for the coordinates might not be stored in the memory. Alternatively, corresponding radiation values and radiation-intensity values may be stored in a serial manner that corresponds to a serial numeration of the microarray spots. The serial numbers may be associated with known x- and y-coordinates of the microarray spots. Similar to the storage scheme described above, the x- and y-coordinate information for the microarray spots is preserved, although the actual values for the coordinates might not be stored in the memory. Accordingly, a relatively small memory might be used for embodiments of the present invention.

The intensity of radiation 255 may be modulated according to a number of schemes by intensity modulator 210. For example, the intensity of the radiation may be continuously modulated, step wise modulated (see, for example, FIG. 10 below and the description thereof), randomly modulated or the like. Further, the intensity of the radiation may be modulated linearly or non-linearly (e.g., exponentially, logarithmically, etc.). According to one intensity-modulation scheme, for each microarray spot, the radiation intensity is modulated from at or below an intensity level that is associated with a threshold measurement level of the A/D converter to an intensity level that is associated with the intermediate range or higher (e.g., above or below the saturation level) of the A/D converter. As each microarray spot may have a different target concentration, the radiation intensity used to place the radiation from the microarray spots in the intermediate range of the A/D converter, may differ. For example, whereas radiation values stored in the memory might be in the intermediate measurement range of the A/D converter, the radiation-intensity values stored in the memory may vary by relatively large amounts compared to the radiation values. An example of this variation is shown in Table 1 below.

Subsequent to storing the radiation values and their associated radiation-intensity values in the memory, the radiation values are normalized by their associated radiation-intensity value and scaled by a highest radiation-intensity value that is stored in the memory. Alternatively, this might be viewed as scaling the radiation values with a highest radiation intensity value that is divided (or normalized) by the radiation-intensity values. Table 1 below includes a number of exemplary excitation values (i.e., radiation-intensity values for fluorescent excitation) and their associated exemplary emission values (e.g., radiation values associated with fluorescent emission) for a number of sample spots. Table 1 also includes a column of normalized emission values that are normalized by their corresponding excitation values and are scaled by a highest excitation value (e.g., 200 according to the example being considered). Controller 230 and/or processor 245 may be configured to identify the highest radiation-intensity value stored in memory, normalize and scale the emission values, and may control the storage of these values in the memory.

TABLE 1

| Sample Spots | Excitation Values | Emission values | Normalized-Emission Values |
|---|---|---|---|
| Sample Spot 1 | 50 | 100 | (200/50) × 100 = 400 |
| Sample Spot 2 | 75 | 90 | (200/75) × 90 = 240 |
| Sample Spot 3 | 200 (highest) | 95 | (200/200) × 95 = 95 |
| Sample Spot 4 | 20 | 115 | (200/20) × 115 = 1150 |
| Sample Spot 5 | 45 | 105 | (200/45) × 105 = 467 |
| Sample Spot 6 | 5 | 115 | (200/5) × 115 = 4600 |

According to the example being considered, at least one of the of the normalized-emission values in the right-most column of Table 1 exceeds the measurement range of A/D converter 235. For example, the measurement range of A/D converter 235 might be a 0 to +1 volt measurement range (i.e., threshold voltage to saturation voltage) and might have a twelve-bit output. As the largest number represented by a twelve-bit binary number is 4095, the normalized-emission value 4600 for sample spot 6 exceeds the measurement range of the A/D converter. That is, the normalized-emission value 4600 may not be expressed by a twelve-bit word, but may be expressed as a thirteen-bit word or longer word. Moreover, the normalized-emission value for sample spot 6 is associated with a normalized-input voltage greater than +1 volt (i.e., saturation voltage of the A/D converter). Accordingly, for sample spot 6, the normalized-input voltage and the normalized emission value exceed the measurement range of A/D converter 235. Accordingly, for the example being considered, the microarray image formed in digital space from the normalized-emission values is independent a hardware constraint of detector 220, and more specifically is independent of the hardware constraint of the A/D converter. As mentioned briefly above, the normalized-emission values shown in Table 1 are the image spots of a microarray image in digital space, such as the digital space of a computer. Accordingly, via the embodiments of the present invention described herein, a microarray image (in digital space) of a microarray may be generated in a single scan of the microarray as a relatively complete set of digital-image data may be collected and normalized to a range that exceeds the measurement range of A/D converter 235.

Figure 7:
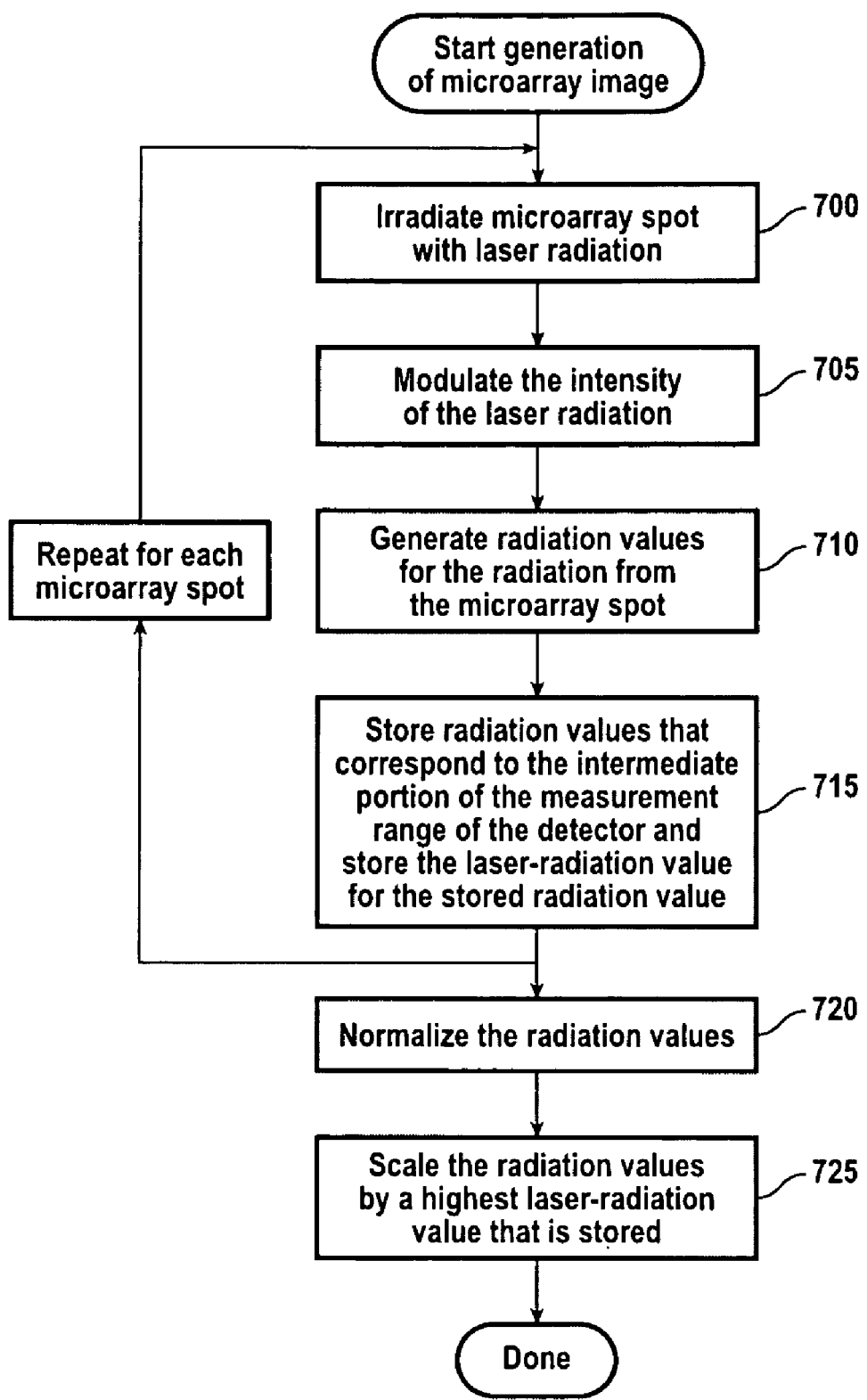
FIG. 7 is a high-level flow chart having steps for generating a microarray image according to an embodiment of the present invention.

FIG. 7 is a high-level flow chart having steps for generating an image of a sample in digital space according to an embodiment of the present invention. The sample might be a biological sample (e.g., a microarray, a tissue sample, a plant sample, etc.), a fluid sample, a chemical sample, or a variety of other sample types. As described above, an image of a sample includes a number of image spots of the sample spots of the sample. The image spots may be represented by digital values in digital space as described above. It should be realized that the steps shown in FIG. 7 are not limiting on the invention as recited in the claims. Other techniques having fewer, substitute, and/or additional steps are within the purview of the invention and will be readily apparent to those of skill in the art. At 700, a sample spot of a sample is irradiated with stimulus radiation, such as laser radiation. At 705, the intensity of the stimulus radiation is modulated. The intensity of the stimulus radiation may be modulated from at or below an intensity level that is associated with a threshold measurement level of a detector (e.g., an A/D converter) to an intensity level that is associated with an intermediate range or higher (e.g., below or above a detector-saturation level) of the detector. In response to being irradiated with the stimulus radiation that has a varying intensity, radiation from the sample spots has a changing intensity. The radiation from the sample spots might include fluorescent radiation, back-scattered radiation, transmitted radiation, or the like. At 710, the detector generates radiation values from the received radiation. The detector may include a photodetector that is configured to generate analog-radiation values in response to receiving the radiation, and may include an A/D converter that is configured to digitize the analog-radiation values to generate digital-radiation values. The radiation values may include these digital-radiation values. As the radiation from the sample spots has a changing intensity, the radiation values generated by the detector from this radiation have changing radiation values. At 715, the radiation values are monitored and a radiation value that is in the intermediate portion of the measurement range of the detector is stored in a memory. Also stored in the memory is a stimulus-radiation value for the stimulus radiation that produced the radiation for the radiation value that is stored in memory. Steps 700-715 are repeated for each sample spot. The sample spots of the sample may be irradiated in a raster scan pattern or other pattern a single time to generate the radiation values. At 720, each radiation value that is stored in memory, is divided (or normalized) by its associated stimulus-radiation value that is stored in memory. At 725, each response value that is normalized is multiplied by the highest of the stimulus-radiation values that are stored in memory to generate the image spots in digital space of the sample image. This multiplication step is sometimes referred to as a scaling step. At least one of the image spots (i.e., the normalized and scaled radiation values) exceeds the measurement range of the A/D converter. As described in detail above, at least one of the image spots may not be expressed by a binary word generated by the A/D converter, but may expressed by a longer binary word (i.e., a binary word having a larger numbers of bits than the binary words generated by the A/D converter). As at least one of the image spots, expressed in binary, exceeds the bit width of binary words generated by the A/D converter, the image spots are said to be independent of the hardware constraint of the A/D converter. Moreover, as these image spots are independent of the hardware constraint of the A/D converter, these image spots may be generated in a single scan of the sample, as compared to multiple scans of the sample using a traditional technique.

According to some embodiments, each sample spot is irradiated by radiation of two or more colors according to the steps described above. For example, each row of microarray spots of a microarray might be irradiated by radiation (e.g., laser radiation) of a first wavelength in a first raster scan of a row, and irradiated by radiation (e.g., laser radiation) of a second wavelength in a second raster scan of the row. Two microarray images might be formed from these different radiation wavelengths.

Figure 8:
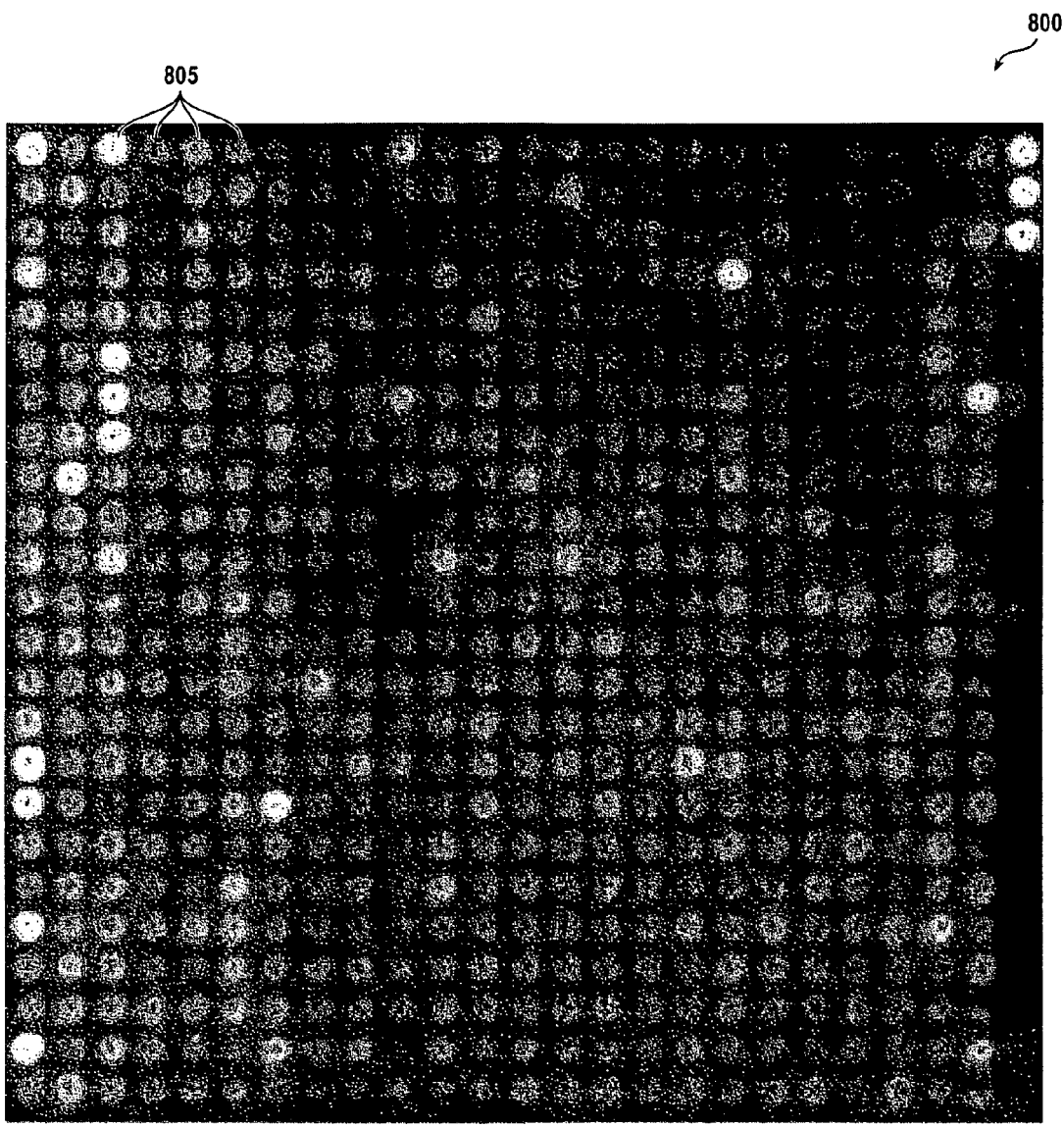
FIG. 8 is a simplified image of a microarray and includes a number of image spots of microarray spots having various radiation intensities.

FIG. 8 is a simplified image 800 of a microarray and has of a number of image spots 805 (digital image data) of microarray spots having a various brightness levels that might be generated by the foregoing described steps and/or deconvolution steps, such as the application of various mathematical functions as described above. The image spots of the microarray image of FIG. 8 might have a relatively greater brightness variation than the image spots of, for example, the microarray image of FIG. 1. For example, the brightness variation of the image spots of FIG. 8 may be relatively large subsequent to normalization, scaling, and/or the application of other deconvolution steps. According to some embodiments, as the range of brightness of the image spots might be relatively large, microarray images are graphically represented in pseudo-color, wherein different colors represent the various brightness levels or various brightness ranges. Pseudo-colors might be used for graphical representation for brightness levels as brightness levels represented in pseudo-color may be easier to visually discern than brightness levels represented in gray-scale.

Figure 9:
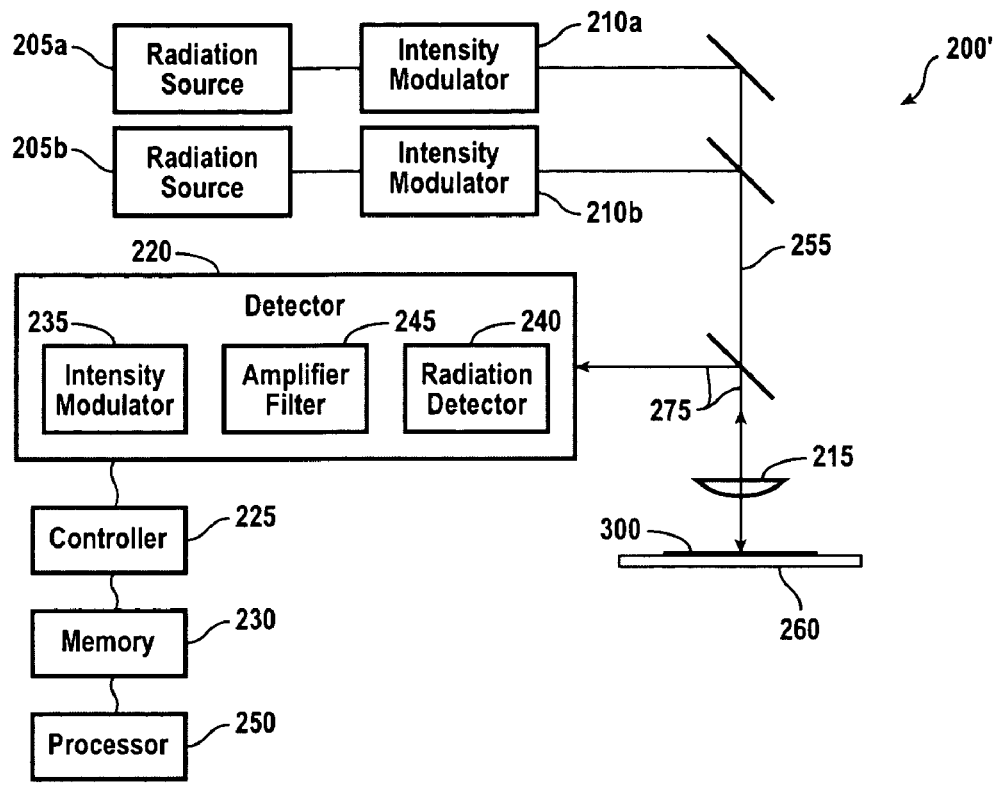
FIG. 9 is a simplified block diagram of a imaging system having two lasers and two intensity modulators respectively associated with the lasers according to another embodiment of the present invention.

FIG. 9 is a simplified block diagram of a imaging system 200' having two radiation sources (e.g., two lasers) 205a and 205b and two intensity modulators 210a and 210b that are respectively associated with the radiation sources according to another embodiment of the present invention. Imaging system 200' differs from embodiments of imaging systems 200 described above in that imaging system 200' includes two radiation sources and two intensity modulators as compared with the one radiation source and one intensity modulator of imaging system 200. Each radiation source is configured to irradiate a microarray or other sample for image generation as described above. The radiation sources are configured to generate radiation of different wavelengths or different combinations of wavelengths (i.e., multi-spectral radiation). According to some embodiments, multi-spectral radiation (e.g., blackbody radiation or the like) is filtered prior to being directed to a microarray or other sample to limit the spectral width of the radiation. The radiation sources may be lasers that may include a frequency doubled YAG laser and a diode laser (e.g., a red diode laser) or other laser types.

Figure 10:
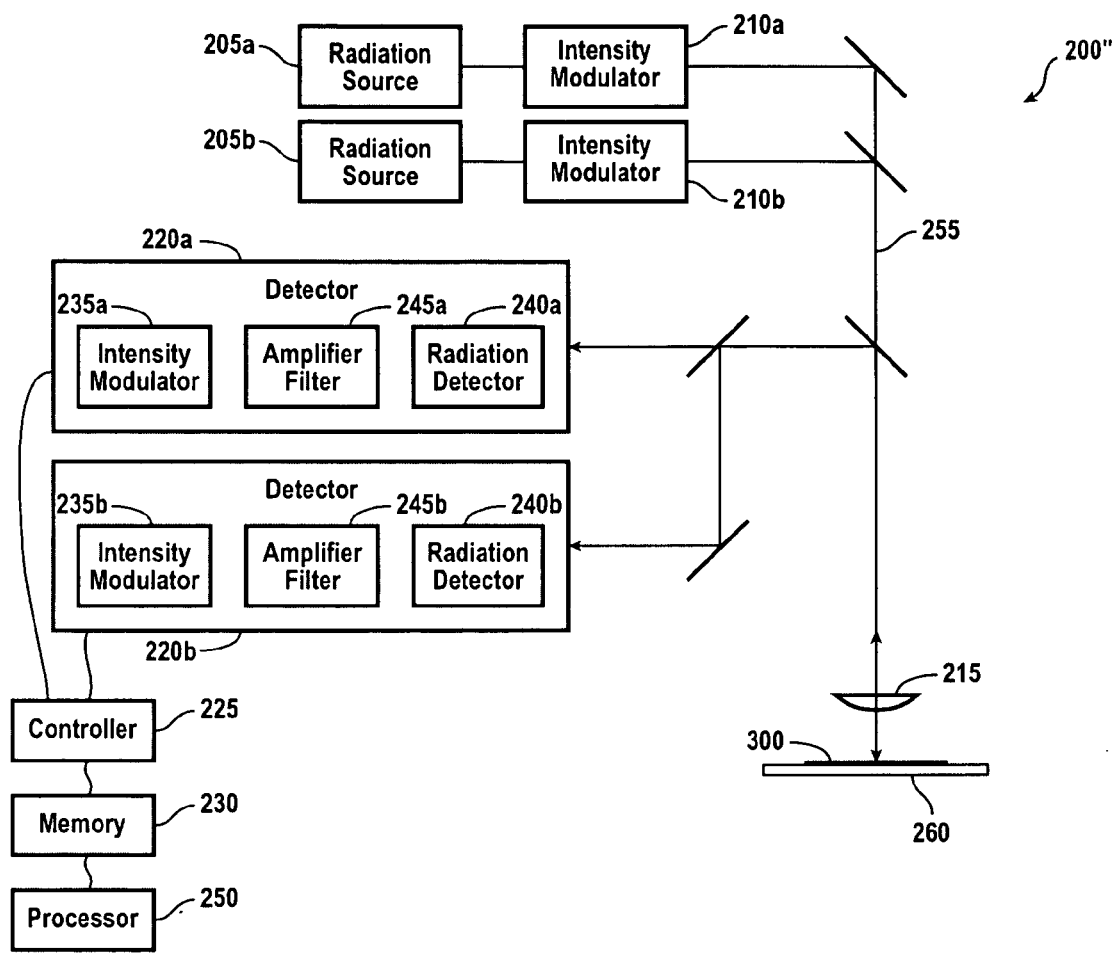
FIG. 10 is a simplified block diagram of an imaging system having two lasers and two detectors respectively associated with the lasers according to another embodiment of the present invention.

FIG. 10 is a simplified block diagram of a imaging system 200" having two radiation sources 205a and 205b and two detectors 220a and 220b that are respectively associated with the radiation sources according to another embodiment of the present invention. Imaging system 200" differs from imaging systems 200 and 200' in that imaging system 200" includes two detectors rather than one detector. Each detector is configured to detect the radiation from the microarray spots that is associated with one of the radiation sources. Detector 220a may include a radiation detector 240a, an amplifier-filter module 245a, and an A/D converter 235a, and detector 220b may include a radiation detector 240b, an amplifier-filter module 245b, and an A/D converter 235b. Each detector of imaging system 200' is configured to operate as described above.

Figure 11:
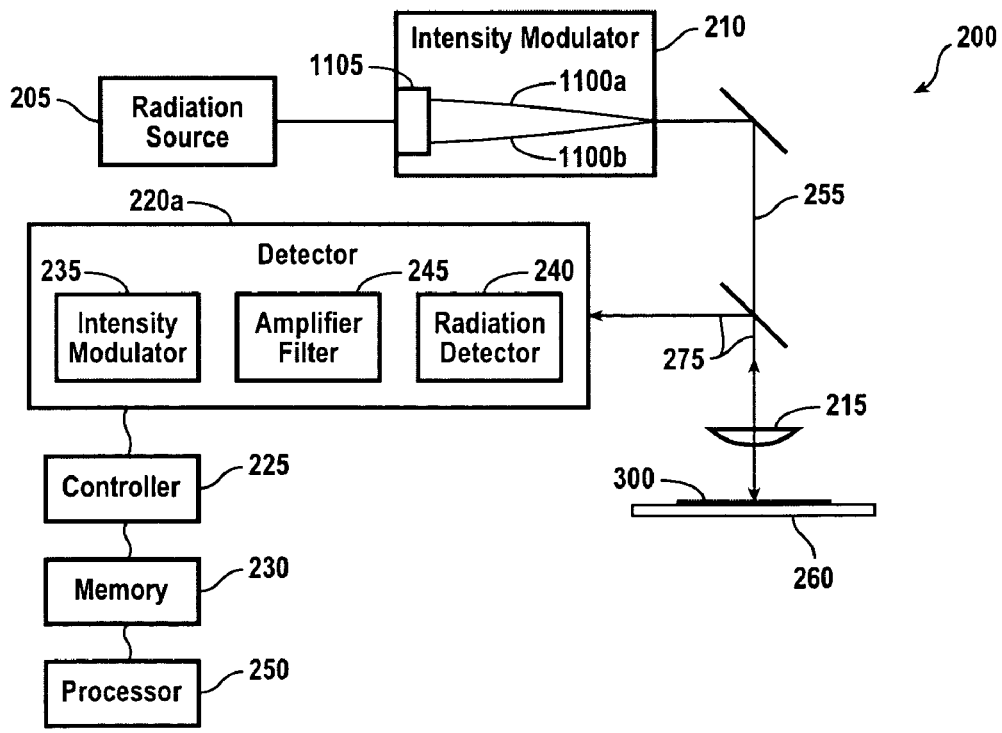
FIG. 11 is a simplified schematic of the intensity modulator according to another embodiment of the present invention.

As described above, stimulus radiation configured to irradiate a sample may be continuously modulated, step wise modulated, randomly modulated or the like. According to a step wise modulation embodiment, intensity modulator 210 is configured to modulate the intensity of radiation 255 through a discrete number of intensities. Intensity modulator 210 might be configured to modulate the intensity of radiation 255 through two, three or more discrete intensities. For example, according to a step wise attenuation scheme, the intensity modulator may be configured to transmit to a sample radiation from radiation source 105 that is un-attenuated and attenuated by a given amount (e.g., attenuated by nine-tenths, i.e., transmit one-tenth of received radiation from the radiation source). According to another step wise attenuation scheme, the intensity modulator may be configured to transmit to a sample radiation that is un-attenuated, the radiation attenuated by one-third, and the radiation attenuated by two-thirds. It should be understood that these attenuation amounts (i.e., intensities) are exemplary and that other discrete intensity levels might be used in accordance with embodiments of the present invention. Intensity modulator 210 may include a variety of means for varying the intensity of radiation 255 in a step wise manner. For example, the intensity modulator might include two, three, or more optical cables (e.g., fiber optic cables) having different attenuations respectively associated with the cables. For example, FIG. 11 shows intensity modulator 210 having two optical cables 1100a and 1100b that are configured to irradiate a sample with different radiation intensities according to one embodiment of the present invention. Optical cable 1100a might be configured to transmit un-attenuated radiation, whereas optical cable 1100b might be configured to attenuate the intensity of the radiation by a select amount (for example nine-tenths; i.e., transmit one-tenth of received radiation 255). For a three optical cable attenuation module, a first optical cable might be configured to provide essentially no attenuation to received radiation, a second optical cable might be configured to attenuate the radiation intensity by one-third, and a third optical cable might be configured to attenuate the radiation intensity by two-thirds. While the foregoing described optical cables are described as being configured to attenuation radiation intensities by select amounts, according to an alternate embodiment, the optical cables might not be configured to attenuate received radiation intensity, but might be optically coupled to attenuators that are configured to provide attenuation of received radiation by select amounts.

According to one embodiment, radiation from radiation source 205 might be directed into the optical cables by an optical switch 1105. Optical switch 1105 might be a Q-switch, an electro-optic switch, such as a y-fiber switch, or other switch type. Optical switch 1005 might alternatively (or additionally) include an occluder (e.g., coupled to a piezo-electric device) configured to occlude radiation from or to one or more optical cables. For example, the occluder might be configured to occlude optical cable 1100a or 1100b at any given time.

According to one embodiment, for each sample spot of a sample, a first optical cable (e.g., optical cable 1100a) that is configured to provide essentially no attenuation is occluded while a second optical cable (e.g., optical cable 1100b) that provides a given amount of attenuation irradiates a sample. If radiation from a sample spot is within a select measurement range of A/D converter 235 (e.g., at or above the lower 10%, the lower 20%, the lower 30%, etc. of the measurement range of the A/D converter), a radiation value for this radiation might be stored in memory along with the state of the occluder. The stimulus-radiation value for this radiation value might also be stored in memory. If the radiation is not within the select measurement range, the second optical cable (e.g., optical cable 1100b) might be occluded while the first optical fiber irradiates the sample. The radiation value for this radiation might be stored along with the state of the occluder. The stimulus-radiation value for this radiation value might also be stored in memory. The attenuation values of the optical cables (or other attenuation devices) may be used to normalize the radiation values stored in memory. While the forgoing describes a two optical cable technique for step wise attenuation of radiation for sample irradiation, the forgoing technique might be used in a similar manner with more than two optical cables having a variety of attenuation amounts.

According to one embodiment, measured attenuations values for attenuators (e.g., optical cables) that are included in imaging systems that are manufactured are stored in their respective imaging systems. Storing attenuation values provides that each imaging system manufactured might include attenuators that have varying attenuation values, but the imaging system may have similar (or substantially the same) operation characteristics. As the various sets of attenuations included in different imaging systems might have different attenuation values, relatively inexpensive attenuators might be used. That is, as the sets of attenuators might need not have the same attenuation values, the costly task of manufacturing (or purchasing) matching sets of attenuators might be avoided.

It should also be understood that the examples and embodiments described herein are for illustrative purposes only, and that various modifications or changes in view thereof will be suggested to persons skilled in the art and are to be included within the spirit and purview of this application and scope of the appended claims. For example, while imaging systems are described above that include one or two radiation sources, such as laser or other sources, other embodiments of the invention may include more than two radiation sources. Therefore, the above description should not be taken as limiting the scope of the invention as defined by the claims.

What is claimed is:

1. A method of measuring a response to a stimulus of a plurality of samples spots of a sample using a measuring system having a measurement range to generate an image of the sample in digital space, the method comprising:

for each sample,
while measuring the response, varying the stimulus to include at least one stimulus value where the measured response corresponds to a value in an intermediate portion of the measuring range, storing a value of the measured response that corresponds to a value in the intermediate portion of the measurement range, and the stimulus value that produced that value of the measured response, dividing each stored value of the measured response by the corresponding stimulus value to provide a normalized-response value, and for each normalized-response value, multiplying each normalized-response value by a highest stimulus value that is stored to generate the image, wherein these normalized-response values that are multiplied by the highest stimulus value that is stored are referred to as the image spots.

2. The method of claim 1, wherein the image spots form the image in digital space.

3. The method of claim 1, wherein the steps of varying the stimulus and storing the value of the measured response are performed in one scan of the sample.

4. The method of claim 3, wherein the scan includes a raster scan of each row of the sample spots.

5. The method of claim 1, wherein the image includes a microarray image of a microarray.

6. The method of claim 1, wherein the measuring system includes an A/D converter having a particular number of bits that accommodates a particular range of response values.

7. The method of claim 6, wherein at least one of the image spots has a number of bits that exceeds the particular number of bits of the A/D converter.

8. The method of claim 1, wherein a variation of the measured responses over the plurality of samples exceeds the measurement range.

9. The method of claim 1, wherein varying the stimulus includes increasing the stimulus over a range.

10. The method of claim 9, wherein increasing the stimulus includes increasing the intensity of laser radiation.

11. The method of claim 1, wherein for multiple ones of the plurality of sample spots, the value in the intermediate portion of the measurement range is approximately the same value.

12. The method of claim 1 wherein:
the samples spots are regions having probes hybridized with targets having fluorescent tags;
the stimulus is visible or UV optical radiation; and
the response is a level of fluorescent emission.

13. The method of claim 12, wherein the stimulus is laser radiation.

14. The method of claim 1 wherein:
the stimulus is electromagnetic radiation; and
the response is a level of reflected radiation or transmitted radiation.

15. A method of acquiring image-response values for an extended sample subjected to a stimulus to generate an image in digital space that includes the image-response values, the method comprising:
for each of a plurality of spots,
subjecting the sample to a plurality of stimulus values in a single scan of the spots,
measuring corresponding response values,
determining a stimulus value that provides a response value within a desired range,
storing the stimulus value, so determined, and the response value provided by that stimulus value,
providing a normalized data set for the plurality of spots where each spot's normalized value represents a ratio of the stored response value and the corresponding stimulus value; and
multiplying the normalized values by a highest stored stimulus value, and these values are the image-response values.

16. The method of claim 15, wherein the desired range is an intermediate range of an A/D converter having a particular number of bits that accommodates a particular range of response values, and at least one of the image-response values has a number bits that exceeds the particular number of bits of the A/D converter.

17. A method for generating a microarray image of a sample that includes a plurality of microarray spots irradiated with laser radiation, such that radiation from each microarray spot is a response to being irradiated, the method comprising:
for each microarray spot in a single scan of the microarray:
varying an intensity value of the laser radiation within a range of values,
storing a radiation value for the radiation, and a corresponding intensity value for that radiation value, wherein the radiation value is below a saturation level of a detector, and
dividing the stored radiation value by the stored intensity value to generate a normalized-radiation value; and
multiplying the normalized-radiation values by a highest radiation value that is stored.

18. The method of claim 17, wherein the detector includes an A/D converter configured to generate the radiation values, and the saturation level is a saturation level of the A/D converter.

19. The method of claim 18, wherein the normalized-radiation values multiplied by the highest radiation value this is stored are independent of a measurement range of the A/D converter.

20. The method of claim 17, wherein the stored radiation values are in a central portion of a measurement range of the detector.

21. The method of claim 17, wherein the stored radiation values vary by about +/−20%.

22. The method of claim 17, wherein the detector includes a radiation-detection that is at least one of a photomultiplier tube, an avalanche photodiode, a CCD (charge coupled device) array, a CMOS (complementary metal oxide) array.

23. The method of claim 17, wherein the stored radiation values are approximately the same.

24. The method of claim 17, wherein the laser radiation is excitation-laser radiation, and the radiation is fluorescent radiation.

25. The method of claim 24, wherein the excitation-laser radiation has a first wavelength and a second wavelength.

26. The method of claim 25, wherein the first wavelength is a red wavelength and the second wavelength is a green wavelength.

27. The method of claim 25, wherein:
the microarray image includes a first microarray image and a sub-microarray image,
the first microarray image is associated with the first wavelength, and
the sub-microarray image is associated with the second wavelength.

28. The method of claim 17, wherein the radiation is back-scattered radiation.

29. The method of claim 17, wherein the step of storing the radiation value includes storing the radiation values and the intensity values in a memory at memory addresses that correspond to coordinate positions of the microarray spots on the sample.

30. The method of claim 17, further comprising digitally operating on the normalized-radiation values with a mathematical function.

31. An image generator for generating a digital-space image of a sample comprises:
- a radiation source configured to generate radiation and irradiate sample spots of the sample, wherein the sample spots radiate in response to being irradiated;
- a modulator configured to modulate an intensity of the radiation;
- a detector having a measurement range and configured to generate radiation values from the radiation from the sample spots;
- a memory configured to store a radiation value that corresponds to an intermediate portion of the measurement range, and a radiation value for the generated radiation that corresponds to that radiation value; and
- a processor configured generate image spots of the digital-space image by normalizing the stored radiation values by their associated radiation values of the generated radiation and multiplying these values by a highest radiation value of the generated radiation this is stored the digital-space image.

32. The generator of claim 31, wherein the detector includes an analog-to-digital (A/D) converter configured to generate the radiation values, and the intermediate portion of the measurement range is an intermediate portion of the measurement range of the A/D converter.

33. The generator of claim 32, wherein the A/D converter has a particular number of bits that accommodates a particular range of radiation values.

34. The generator of claim 33, wherein at least one of the image spots has a number bits that exceeds the particular number of bits of the A/D converter.

35. The method of claim 32, wherein the image spots are independent of a measurement range of the A/D converter.

36. The generator of claim 32, wherein the detector includes a radiation-detection configured to detect the radiation, and the radiation detector includes at least one of a photomultiplier tube, an avalanche photodiode, a CCD (charge coupled device) array, and a CMOS (complementary metal oxide) array.

37. The generator of claim 36, and further comprising an amplifier-filter module configured to amplify and filter output of the radiation detector and provide amplified and filtered output to the A/D converter.

38. The generator of claim 31, wherein the processor is configured to multiply the normalized-radiation values by a highest laser-radiation value to generate the microarray image.

39. The generator of claim 31, wherein the processor is a RISK (reduced instruction set) microprocessor.

40. The generator of claim 31, wherein the intensity modulator includes at least one of an electrooptic modulator disposed between a pair of crossed polarizers, an acoustooptic modulator, and a controllable variable-neutral-density filter.

41. The generator of claim 31, and further comprising a lens system configured to focus the laser radiation on the sample spots and collect the radiation from the sample spots for collection by the detector.

42. The generator of claim 31, and further comprising a second laser configured to irradiate the sample spots with laser radiation having a wavelength different from the laser radiation of the first mentioned laser to generate a second microarray image.

* * * * *